(12) United States Patent
Araki et al.

(10) Patent No.: US 10,036,724 B2
(45) Date of Patent: Jul. 31, 2018

(54) GAS SENSOR

(71) Applicant: DENSO CORPORATION, Kariya, Aichi-pref. (JP)

(72) Inventors: Takashi Araki, Kariya (JP); Keigo Mizutani, Kariya (JP); Mitsunobu Nakatou, Kariya (JP)

(73) Assignee: DENSO CORPORATION, Kariya (JP)

( * ) Notice: Subject to any disclaimer, the term of this patent is extended or adjusted under 35 U.S.C. 154(b) by 245 days.

(21) Appl. No.: 14/912,989

(22) PCT Filed: Aug. 21, 2014

(86) PCT No.: PCT/JP2014/071897
§ 371 (c)(1),
(2) Date: Feb. 19, 2016

(87) PCT Pub. No.: WO2015/025924
PCT Pub. Date: Feb. 26, 2015

(65) Prior Publication Data
US 2016/0209354 A1    Jul. 21, 2016

(30) Foreign Application Priority Data
Aug. 21, 2013  (JP) .................................. 2013-171109

(51) Int. Cl.
*G01N 27/419* (2006.01)
*G01N 27/409* (2006.01)
(Continued)

(52) U.S. Cl.
CPC ......... *G01N 27/419* (2013.01); *G01N 27/409* (2013.01); *G01N 27/4071* (2013.01); *G01N 27/41* (2013.01)

(58) Field of Classification Search
CPC .. G01M 15/10; G01M 15/102; G01M 15/104; G01N 27/404–27/407;
(Continued)

(56) References Cited

U.S. PATENT DOCUMENTS

| | | | |
|---|---|---|---|
| 4,655,901 A | 4/1987 | Mase et al. | |
| 5,360,528 A * | 11/1994 | Oh | G01N 27/419 204/192.1 |

(Continued)

FOREIGN PATENT DOCUMENTS

| | | |
|---|---|---|
| JP | 60-36949 | 2/1985 |
| JP | 6-213864 | 8/1994 |

(Continued)

OTHER PUBLICATIONS

International Preliminary Report on Patentability (4 pages) dated Mar. 3, 2016, issued in corresponding Japanese Application No. PCT/JP2014/071897 and English translation (10 pages).

(Continued)

*Primary Examiner* — Gurpreet Kaur
(74) *Attorney, Agent, or Firm* — Nixon & Vanderhye P.C.

(57) ABSTRACT

A gas sensor is provided which constitutes a pump cell 3 and a sensor cell 5 using a single solid electrolyte body 2, a pump electrode 30, a sensor electrode 50, and a reference electrode 80 and is designed to decrease power consumed by a heater and permit a size thereof to be reduced. A ratio of a minimum distance L2 between the pump electrode 30 and the sensor electrode 50 to a thickness d of the solid electrolyte body 2 is set to be three or more, thereby enabling the gas sensor 1 to make the pump cell 3 and the sensor cell 5 using the single solid electrolyte body 2, the pump electrode 30, the sensor electrode 50, and the reference electrode 80. Only either of the gas chamber or the reference gas chamber is, therefore, located between the solid electrolyte body and (Continued)

the heater, thereby decreasing distances of the pump cell and the sensor cell to the heater. This facilitates the ease with which the heater heats up the pump cell and the sensor cell.

5 Claims, 6 Drawing Sheets

(51) Int. Cl.
G01N 27/41 (2006.01)
G01N 27/407 (2006.01)

(58) Field of Classification Search
CPC .... G01N 27/409; G01N 27/419; G01N 27/41; F01N 2560/00–2560/20; F01N 2550/00–2550/24; F02D 4/123; F02D 4/1454

See application file for complete search history.

(56) References Cited

U.S. PATENT DOCUMENTS

| | | | |
|---|---|---|---|
| 5,676,811 A | 10/1997 | Makino et al. | |
| 6,045,673 A | 4/2000 | Kato et al. | |
| 6,551,497 B1 * | 4/2003 | Gao | G01N 27/4065 204/425 |
| 2001/0022365 A1 | 9/2001 | Murade | |
| 2002/0104758 A1 | 8/2002 | Mizutani et al. | |
| 2002/0195338 A1 | 12/2002 | Mizutani et al. | |
| 2004/0004221 A1 | 1/2004 | Murade | |
| 2004/0045824 A1 | 3/2004 | Hada et al. | |
| 2004/0050695 A1 | 3/2004 | Haraguchi et al. | |
| 2004/0074773 A1 | 4/2004 | Niwa | |
| 2009/0236223 A1 | 9/2009 | Hada et al. | |
| 2013/0092537 A1 | 4/2013 | Mizutani et al. | |
| 2016/0209354 A1 | 7/2016 | Araki et al. | |

FOREIGN PATENT DOCUMENTS

| | | |
|---|---|---|
| JP | 9-105737 | 4/1997 |
| JP | 2000-321238 | 11/2000 |
| JP | 2001-153840 | 6/2001 |
| JP | 2001-330856 | 11/2001 |
| JP | 2002-310987 | 10/2002 |
| JP | 2003-083936 | 3/2003 |
| JP | 2004-093386 | 3/2004 |
| JP | 2004-108788 | 4/2004 |
| JP | 2004-125482 | 4/2004 |
| JP | 2004-125534 | 4/2004 |
| JP | 2004-132840 | 4/2004 |
| JP | 2005-249718 | 9/2005 |
| JP | 2009-036608 | 2/2009 |
| JP | 2009-150719 | 7/2009 |
| JP | 2009-229148 | 10/2009 |
| JP | 2010-048647 | 3/2010 |

OTHER PUBLICATIONS

International Search Report for PCT/JP2014/071897, dated Nov. 18, 2014, 4 pages.

* cited by examiner

| L2 [mm] | d [mm] | L2/d | OUTPUT ERROR |
|---|---|---|---|
| 0.15 | 0.15 | 1.0 | 27.0% |
| 0.30 | 0.15 | 2.0 | 10.0% |
| 0.45 | 0.15 | 3.0 | 2.5% |
| 0.50 | 0.15 | 3.3 | 1.6% |
| 0.60 | 0.15 | 4.0 | 1.0% |
| 0.65 | 0.15 | 4.3 | 1.1% |
| 0.70 | 0.15 | 4.7 | 0.9% |
| 0.90 | 0.15 | 6.0 | 0.8% |
| 1.05 | 0.15 | 7.0 | 0.8% |
| 0.65 | 0.65 | 1.0 | 29.0% |
| 0.65 | 0.33 | 2.0 | 9.0% |
| 0.65 | 0.22 | 3.0 | 2.2% |
| 0.65 | 0.20 | 3.3 | 1.5% |
| 0.65 | 0.15 | 4.3 | 1.0% |
| 0.65 | 0.10 | 6.5 | 0.7% |

GAS SENSOR

This application is the U.S. national phase of International Application No. PCT/JP2014/071897 filed 21 Aug. 2014, which designated the U.S. and claims priority to JP Patent Application No. 2013-171109 filed 21 Aug. 2013, the entire contents of each of which are hereby incorporated by reference.

TECHNICAL FILE

The present invention generally relates to a gas sensor which measures the concentration of a given gas component contained in oxygen-containing gas.

BACKGROUND ART

For instance, Patent Literature 1, as listed below, discloses a gas sensor which is equipped with two solid electrolyte bodies having oxygen ion conductivity and measures the concentration of NOx contained in exhaust gas from automotive vehicles. The solid electrolyte bodies are in the shape of sheet and face each other in a thickness-wise direction thereof. A space exists between the solid electrolyte bodies as a gas chamber into which gas (i.e., the exhaust gas) is admitted. Each of the solid electrolyte bodies has a surface exposed to the gas and an opposite surface exposed to a reference gas such as atmospheric air.

Each of the solid electrolyte bodies has electrodes formed on both the surfaces thereof. One of the solid electrolyte bodies (which will also be referred to as a first solid electrolyte body below) and the electrodes formed on the surfaces thereof constitute a pump cell. The other solid electrolyte body (which will also be referred to as a second solid electrolyte body below) and the electrodes formed on the surfaces thereof constitute a monitor cell and a sensor cell. The pump cell, the monitor cell, and the sensor cell are different in function from each other. These three cells are used to measure the concentration of a given gas component such as NOx contained in gas.

The above gas sensor is also equipped with a heater which works to heat the first and second solid electrolyte bodies up to an activatable temperature thereof. The heater is disposed so that it faces a surface of the first solid electrolyte body which is opposed to the surface thereof facing the second electrolyte body. A space exist between the heater and the first solid electrolyte body as a reference gas chamber into which the reference gas is admitted.

CITATION LIST

Patent Literature

Patent Literature 1
  Japanese Patent First Publication No. 2004-108788

SUMMARY OF THE INVENTION

Problems to be Solved by the Invention

However, the above gas sensor has the reference gas chamber, the first solid electrolyte body, and the gas chamber arranged in an interval between the heater and the second solid electrolyte body, thus resulting in an increase in distance between the heater and the second solid electrolyte body. This causes a problem that the size of the gas sensor is increased.

The long distance between the heater and the second solid electrolyte body in the above gas sensor also results in a difficulty in keeping the temperature of the second solid electrolyte body constant. In other words, it results in a variation in temperature of the second solid electrolyte body. This also results in a variation in temperature of the monitor cell or the sensor cell made by the second solid electrolyte body, which may lead to a difficulty in ensuring a desired accuracy in measuring the concentration of the given gas component. The long distance between the heater and the second solid electrolyte body will also cause a problem that a grate electric power is consumed to heat the solid electrolyte body up to a desired temperature.

The present invention was made in view of the above problems. It is an object to provide a gas sensor which is designed to minimize a variation in temperature of each cell and enables the amount of power consumed by a heater to be decreased and the size thereof to be reduced.

Means for Solving Problem

One aspect of the invention is a gas sensor for measuring a concentration of a given gas component in oxygen-containing gas comprising:

a gas chamber into which said gas is introduced;

a reference gas chamber into which a reference gas is introduced;

a single plate-like solid electrolyte body which has oxygen ion conductivity and is disposed between said gas chamber and said reference gas chamber, the solid electrolyte body having a first major surface facing said gas chamber and a second major surface facing said reference gas chamber;

a plurality of electrodes which are formed on the first major surface of said solid electrolyte body;

a reference electrode which is formed on the second major surface of said solid electrolyte body;

a pump electrode which is one of said electrodes formed on the first major surface of said solid electrolyte body, the pump electrode constituting a pump cell along with said reference electrode and a portion of said solid electrolyte body, the pump cell working to regulate a concentration of oxygen in said gas;

a sensor electrode which is one of said electrodes formed on the first major surface of said solid electrolyte body, the sensor electrode constituting a sensor cell along with said reference electrode and a portion of said solid electrolyte body, the sensor cell through which a current flows which corresponds to a concentration of the given gas component in said gas after the concentration of oxygen is regulated by said pump cell; and a plate-like heater which is located so as to face said solid electrolyte body through said gas chamber or said reference gas chamber, said heater having a given thickness to heat up said solid electrolyte body, wherein dc voltage is applied to said pump cell and said sensor cell, and said current flowing through said sensor cell is measured for measuring the concentration of the given gas component, and wherein a ratio of a minimum distance between said pump electrode and said sensor electrode to a thickness of said solid electrolyte body is three or more.

Beneficial Effects of the Invention

Specifically, the condition where the ratio is three or more is met by setting the minimum distance between the pump electrode and the sensor electrode to be greater than the thickness of the solid electrolyte body. This results in an increased resistance between the pump electrode and the sensor electrode to reduce a leakage of current from the pump electrode to the sensor electrode, thus creating a required flow of electric current required by the pump cell. The condition where the ratio is three or more is also met by setting the thickness of the solid electrolyte body to be smaller than the distance between the pump electrode and the sensor electrode. This results in a decreased resistance between the pump electrode and the reference electrode constituting the pump cell to reduce a leakage of current from the pump electrode to the sensor electrode, thereby decreasing electrical current leaking into the sensor cell. This improves the accuracy in measuring the concentration of the given gas component.

The selection of the ratio of the minimum distance between the pump electrode and sensor electrode to the thickness of the solid electrolyte body to be three or more enables the pump cell which regulates the concentration of oxygen in the gas and the sensor cell which outputs a signal corresponding to the concentration of the given gas component in the gas after the pump cell regulates the concentration of oxygen to be made by the single solid electrolyte body, the plurality of electrodes formed on the first major surface of the solid electrolyte body and the reference electrode formed on the second major surface of the solid electrolyte body.

This causes only either one of the gas chamber and the reference gas chamber to be located between the solid electrolyte body and the heater, thus resulting in a decrease in distance from the pump cell and the sensor cell to the heater. This facilitates the ease with which the heater heats up the pump cell 3 and the sensor cell and also results in a decrease in thickness of the gas sensor, which leads to a decreased size of the gas sensor.

As described above, this disclosure provides the gas sensor which is high in accuracy to measure the concentration of the given gas component.

EMBODIMENTS FOR CARRYING OUT THE INVENTION

First Embodiment

Figure 1:
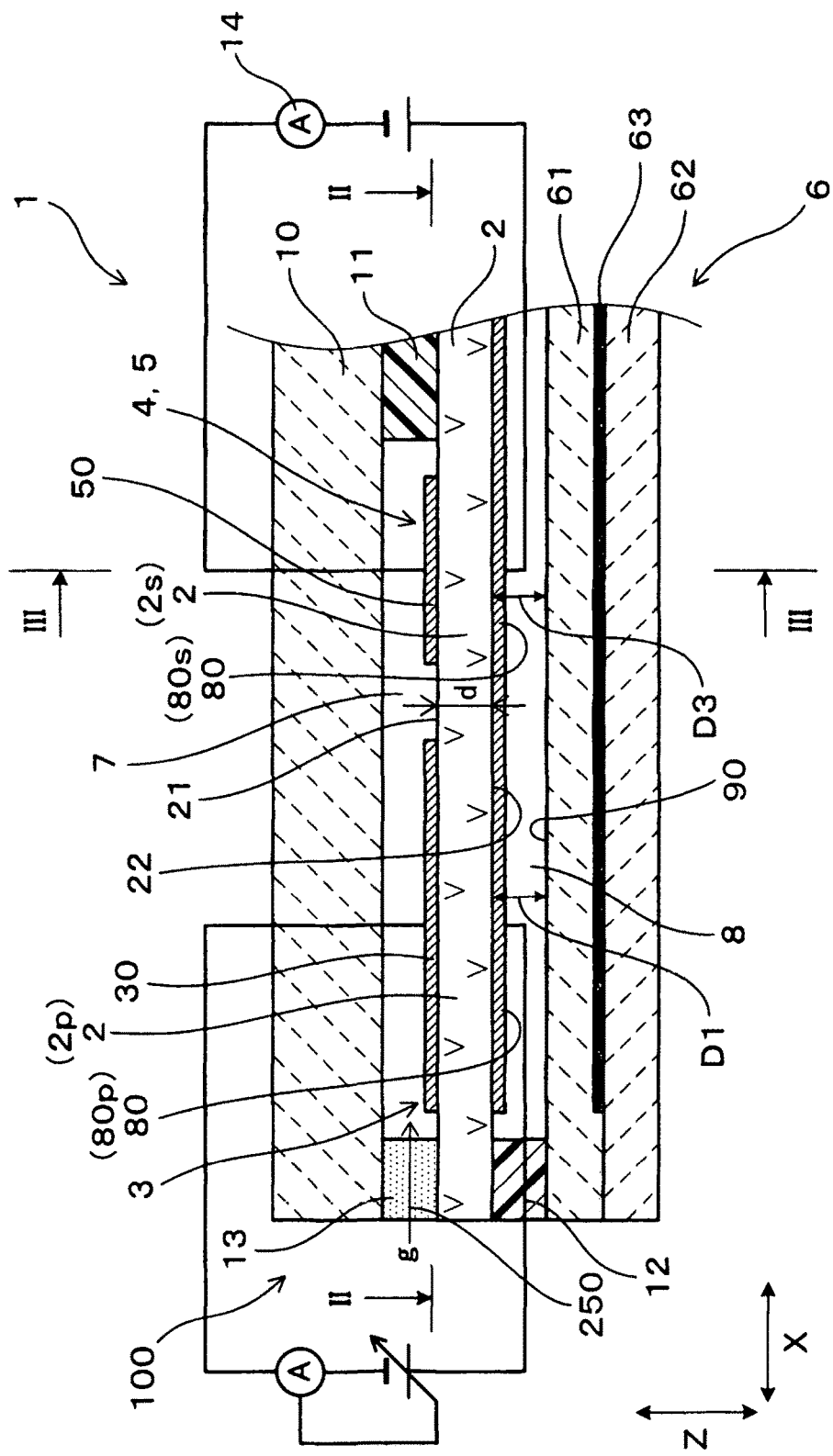
FIG. 1 is a sectional view of a gas sensor in the first embodiment.

A gas sensor 1 of the first embodiment will be described below using FIGS. 1 to 4. The gas sensor 1 is used to measure the concentration of a given gas component contained in oxygen-containing gas g. The gas sensor 1, as illustrated in FIG. 1, includes a gas chamber 7, a reference gas chamber 8, a plate-like solid electrolyte body 2 ($2p$, $2m$, and $2s$), a pump electrode 30, a monitor electrode 40, a sensor electrode 50, a reference electrode 80, a plate-like heater 6 which has a given thickness. The oxygen-containing gas g is inputted to the gas chamber 7. A reference gas is inputted to the reference gas chamber 8.

The solid electrolyte body 2 is interposed between the gas chamber 7 and the reference gas chamber 8. The solid electrolyte body 2 is a plate-like member made of material such as zirconia or ceria having an oxygen ion conductivity.

The solid electrolyte body 2, as illustrated in FIG. 1, has a given thickness d and also has a first major surface 21 and a second major surface 22 which face each other through the thickness d. The pump electrode 30, the monitor electrode 40, and the sensor electrode 50 are formed on the first major surface 21 of the solid electrolyte body 2 which is exposed to the gas chamber 7. The reference electrode 80 is formed on the second major surface 22 of the solid electrolyte body 2 which is exposed to the reference gas chamber 8.

The thickness d of the solid electrolyte body 2 is an average of thicknesses, as measured at five points located in a lengthwise-direction thereof.

The heater 6 works to heat the reference electrode 80 in addition to the pump electrode 30, the monitor electrode 40, the sensor electrode 50, and the solid electrolyte body 2 up to a given temperature required to activate the solid electrolyte body 2. The activation of the solid electrolyte body 2 means that the solid electrolyte body 2 has reached a temperature required to measure the concentration of oxygen or NOx and is operable to decompose NOx into oxygen ions and nitrogen ions.

Figure 3:
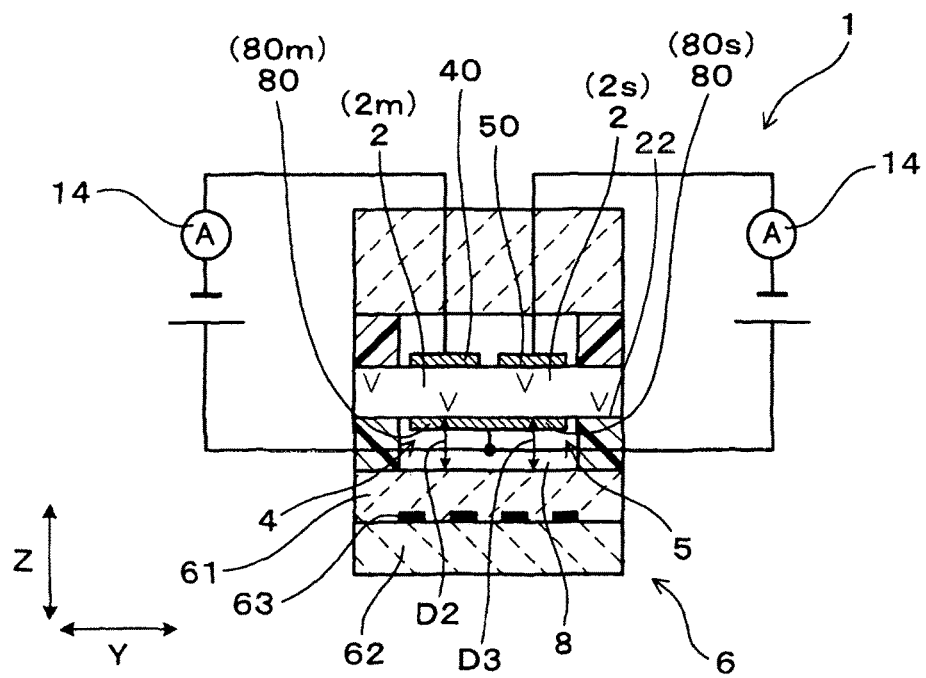
FIG. 3 is a sectional view, as taken along the line in FIG. 1.

The solid electrolyte body 2, the pump electrode 30, and the reference electrode 80 constitute the pump cell 3 working to regulate the concentration oxygen in the gas g. The solid electrolyte body 2, the monitor electrode 40, and the reference electrode 80, as illustrated in FIG. 3, constitute the monitor cell 4 which works to monitor the concentration of oxygen in the gas g after the pump cell 3 regulates the concentration of oxygen in the gas g. The solid electrolyte body 2, the sensor electrode 50, and the reference electrode 80, as illustrated in FIGS. 1 and 3, constitute the sensor cell 5 which works to measure the concentration of the given gas component in the gas g after the pump cell 3 regulates the concentration of oxygen in the gas g. Specifically, the sensor cell 5 outputs a signal indicative of the concentration of the given gas component.

The heater 6 is disposed to face the solid electrolyte body 2 through the reference gas chamber 8.

A distance D1 from a portion $2p$ of the solid electrolyte body 2 which constitutes the pump cell 3 to the heater 6 in the thickness-wise direction of the heater 6 (i.e., the z-direction), a distance D2 from a portion $2m$ of the solid electrolyte body 2 which constitutes the monitor cell 4 to the heater 6 in the thickness-wise direction of the heater 6, and a distance D3 from a portion $2s$ of the solid electrolyte body 2 which constitutes the sensor cell 5 to the heater 6 in the thickness-wise direction of the heater 6 are equal to each other. Specifically, the heater 6 is made up of ceramic-made heater sheet 62, a heater pattern 63 which is formed on the surface of the heat sheet 62 and produces heat when energized, and an insulating layer 61 which covers the heater pattern 63. The distance D1 is a minimum distance between an area of the portion $2p$ constituting the pump cell 3, which is a portion of the major surface 22 of the solid electrolyte body 2, and the major surface 90 of the insulating layer 61 which faces the major surface 22. The distance D2 is, as can be seen in FIG. 3, a minimum distance between an area of the portion 2m constituting the monitor cell 4, which is a portion of the major surface 22 of the solid electrolyte body 2, and the major surface 90 of the insulating layer 61. The distance D3 is a minimum distance between an area of the portion 2s constituting the sensor cell 5, which is a portion of the major surface 22 of the solid electrolyte body 2, and the major surface 90 of the insulating layer 61.

The gas sensor 1 of this embodiment functions as a NOx sensor which measures the concentration of NOx contained in exhaust gas from automotive vehicles. The gas g in this embodiment is, therefore, the exhaust gas from automotive vehicles equipped with an internal combustion engine. The given gas component is NOx. In the case where the concentration of NOx is measured, the whole of the gas sensor 1 is disposed inside a cylindrical casing, not shown, and installed in an exhaust pipe of the automotive vehicle. Specifically, the gas sensor 1 has a tip portion 100 inserted into the exhaust pipe and a rear end portion exposed to air that is the reference gas.

Figure 4:
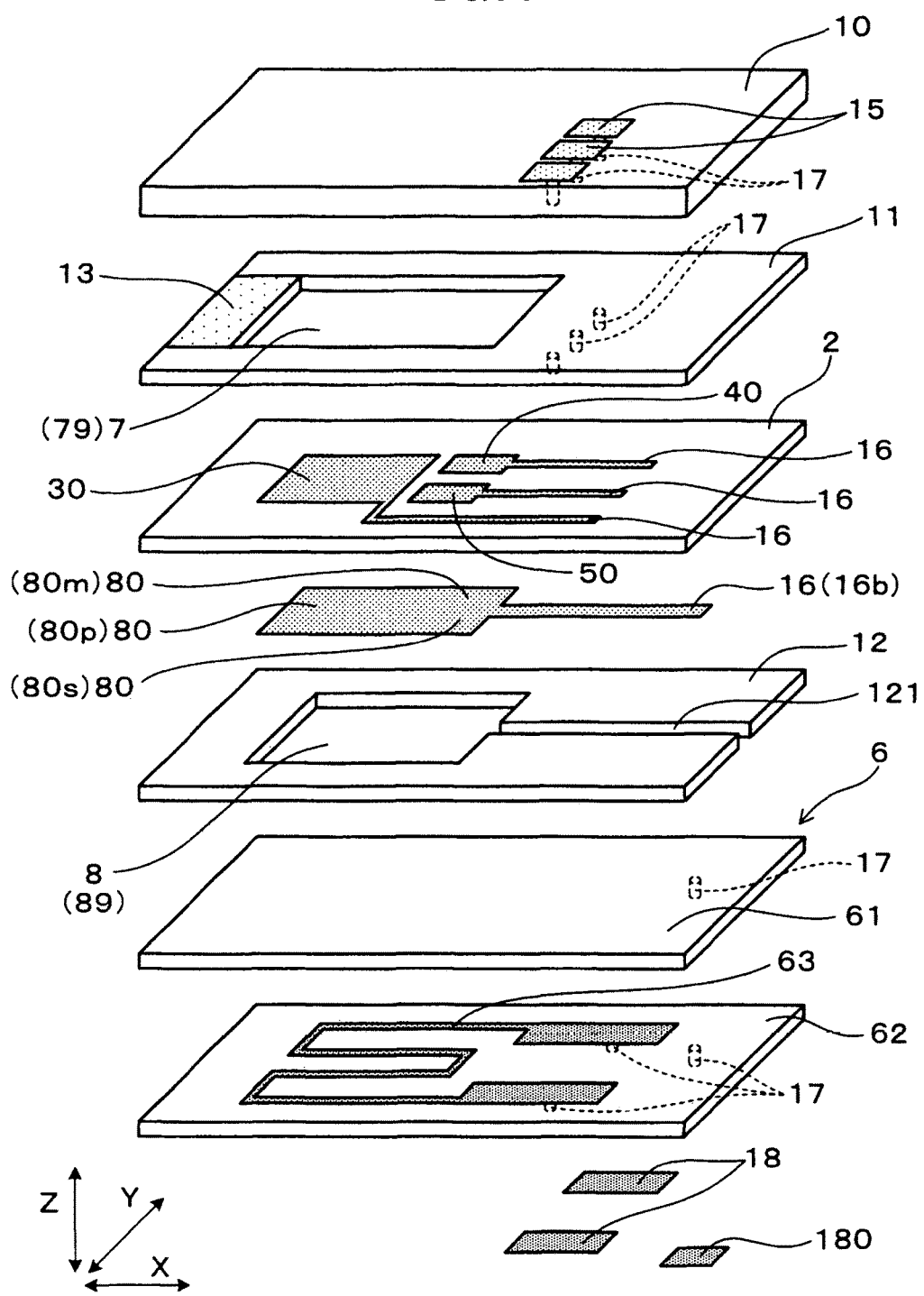
FIG. 4 is an exploded perspective view of a gas sensor in the first embodiment.

The gas sensor 1, as illustrated in FIGS. 1 and 4, has the ceramic-made insulating plate 10, a sheet-like first spacer 11 for defining the gas chamber 7, the solid electrolyte body 2, a sheet-like second spacer 12 for defining the reference gas chamber 8, and the heater 6 for heating the pump cell 3, the monitor cell 4, and the sensor cell 5 which are stacked in the Z-direction.

Figure 2:
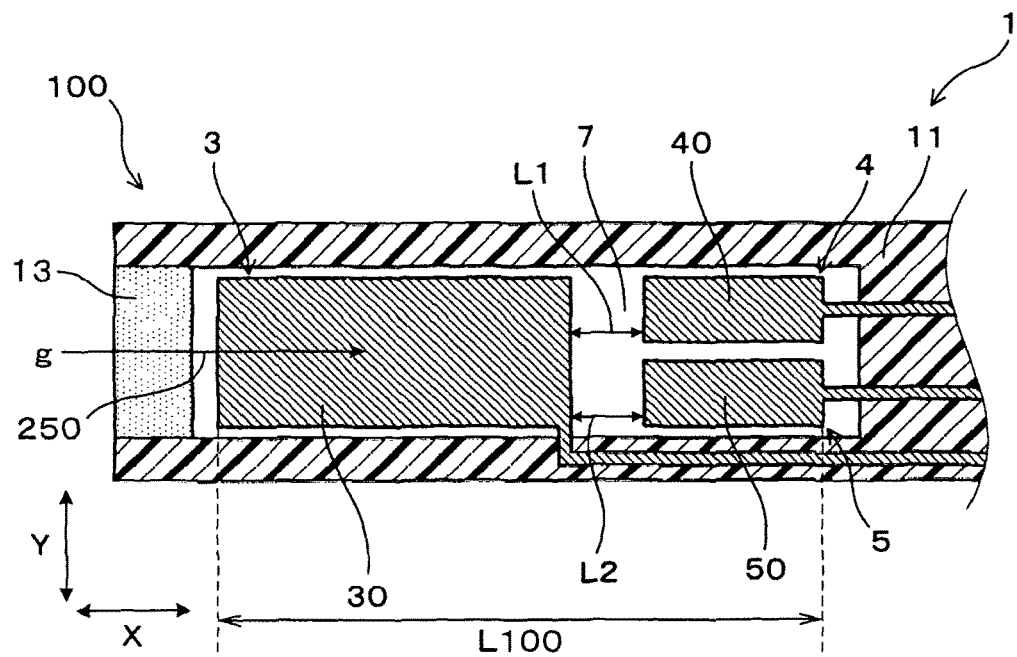
FIG. 2 is a sectional view, as taken along the line II-II in FIG. 1.

The gas chamber 7 is a space into which the exhaust gas (i.e., the gas g) emitted from the automotive vehicle is introduced. The gas g, as illustrated in FIGS. 1 and 2, flows within the gas chamber 7 in a direction, as indicated by an arrow 250. The first spacer 11, as illustrated in FIG. 4, has a cut-out portion 79 formed therein. The cut-out portion 79 defines the gas chamber 7. The first spacer 11 has formed therein a diffusion resistance layer 13 through which the gas g is introduced from the exhaust pipe into the gas chamber 7. The diffusion resistance layer 13 works to restrict the velocity at which the gas g flows therethrough.

The reference gas chamber 8 is a space into which air is introduced as the reference gas in which the concentration of oxygen is constant. The reference gas chamber 8 is defined by a through hole 89 formed in the second spacer 12. The through hole 89 communicates through a passage 121 with an external space outside the gas sensor 1 in which air exists. The passage 121 is formed by a groove extending in a direction X in which the gas g flows (i.e., a direction 250 illustrated in FIGS. 1 and 2 in which the gas g flows in the gas chamber 7). The air is introduced into the reference gas chamber 8 through the passage 121. The first spacer 11 and the second spacer 12 are made of an insulating material such as alumina.

The pump electrode 30 and the monitor electrode 40 are made of a metallic material which is low in activity to decompose the NOx. Specifically, the pump electrode 30 and the monitor electrode 40 are each made by a porous cermet electrode containing gold Au and platinum Pt as major components. The sensor electrode 50 is made of a metallic material which is high in activity to decompose NOx. Specifically, the sensor electrode 50 is made by a porous cermet electrode containing platinum Pt and rhodium Rh.

The pump electrode 30, the monitor electrode 40, the sensor electrode 50, and the reference electrode 80, as illustrated in FIG. 4, have leads 16 which define passage for electric current. The first spacer 11 and the insulating plate 10 have formed therein through holes 17 passing therethrough in the Z-direction. The through holes 17 establish electrical conduction of the pump electrode 30, the monitor electrode 40, and the sensor electrode 50 with the surface of the insulating plate 10. The insulating plate 10 has formed on a plurality of lead-connecting electrodes 15 for electric connections with an external device.

The heater 6 is made up of the ceramic-made heater sheet 62, the heater pattern 63 which is formed on the heater sheet 62 and produces heat when electrically energized, and the insulating layer 61 which covers the heater pattern 63. When supplied with electric power externally, the heater pattern 63 of the heater 6 produces thermal energy to heat each of the pump cell 3, the monitor cell 4, and the sensor cell 5 up to the activating temperature. The heater sheet 62 has pads 18 formed thereon and also has formed therein the through holes 17 through which the heater pattern 63 electrically connects with the pads 18. The reference electrode 80 also electrically connects through the through hole 17 with a lead-connecting electrode 180 formed on the surface of the heater sheet 62.

In order to emit a large amount of oxygen using the pump cell 3, a heat-producing center of the heater pattern 63 is located closer to the pump cell 3. In other words, the heater pattern 63 is designed to heat the pump cell 3, the monitor cell 4, and the sensor cell 5 so that the pump cell 3 will be higher in temperature than the monitor cell 4 and the sensor cell 5.

The solid electrolyte body 2, as illustrated in FIGS. 1 to 3, has the thickness d. The pump electrode 30 and the sensor electrode 50 are located at a minimum distance L2 away from each other. In this embodiment, the gas sensor 1 is designed to have a ratio (L2/d) of the minimum distance L2 to the thickness d of the solid electrolyte body 2 set to 3 or more.

The thickness d of the solid electrolyte body 2 is, as described above, an average of thicknesses, as measured at five points on the plate-like solid electrolyte body 2 given in the lengthwise direction thereof. The minimum distance L2 between the pump electrode 30 and the sensor electrode 50 is an interval between the pump electrode 30 and the sensor electrode 50 in the lengthwise direction of the solid electrolyte body 2 on which the pump electrode 30 and the sensor electrode 50 are formed, that is, in the direction 250 in which the gas g flows.

In other words, the condition where the above ratio is three or more is met by setting the minimum distance L2 between the pump electrode 30 and the sensor electrode 50 to be greater than the thickness d of the solid electrolyte body 2. This results in an increased resistance between the pump electrode 30 and the sensor electrode 50 to reduce a leakage of current from the pump electrode 30 to the sensor electrode 50, thus creating a required flow of electric current required by the pump cell 3.

The condition where the above ratio is three or more is also met by setting the thickness d of the solid electrolyte body 2 to be smaller than the distance L2 between the pump electrode 30 and the sensor electrode 50. This results in a decreased resistance between the pump electrode 30 and the reference electrode 80 constituting the pump cell 3 (i.e., a reference electrode 80p) to reduce a leakage of current from the pump electrode 30 to the sensor electrode 50, thereby decreasing electric current leaking into the sensor cell 5. This improves the accuracy in measuring the concentration of the given gas component.

The ratio of the minimum distance L2 between the pump electrode 30 and the sensor electrode 50 to the thickness d of the solid electrolyte body 2 is, as described above, determined to be three or more, thereby enabling the gas sensor 1 to be made only by the single solid electrolyte body 2. On the solid electrolyte body 2, the pump electrode 30, the monitor electrode 40, the sensor electrode 50, and the reference electrode 80 are formed to make three types of cells: the pump cell 3, the monitor cell 4, and the sensor cell 5.

In terms of reducing the size of the gas sensor 1, it is preferable that the minimum distance L2 is 0.3 mm to 0.7 mm, and the thickness d of the solid electrolyte body 2 is 0.1 mm to 0.3 mm, and that the ratio (L2/d) of the minimum distance L2 to the thickness d is less than or equal to 7.

The respective numerical ranges are specified in terms of the strength of the solid electrolyte body 2 and the functions of the pump cell 3, the monitor cell 4, and the sensor cell 5.

The determination of the concentration of the given gas component (i.e., NOx) of the oxygen-containing gas g is, as described above, achieved by measuring a concentration of oxygen by the monitor cell 4 which still remains in the gas g after being regulated in concentration of oxygen by the pump cell 3, determining through the sensor cell 5 a concentration of oxygen corresponding to the sum of the concentration of the given gas component (i.e., NOx) and the concentration of the residual oxygen, and deriving a difference between an output of the sensor cell 5 and an output of the monitor cell 4 to remove a component indicative of the concentration of the residual oxygen from the output of the sensor cell 5.

In this embodiment, the gas chamber 7 is, as illustrated in FIGS. 1 and 2, formed by a single space defined by the first spacer 11, the insulating plate 10, and the solid electrolyte body 2. This facilitates ease with which the gas g flows within the gas chamber 7, thereby achieving detection of a change in output from the sensor cell 5 which indicates the concentration of the given gas component at a high response rate. The single space which defines the gas chamber 7 has a given thickness in the thickness-wise direction of the heater 6 (i.e., the Z-direction) and a given width. The thickness of the gas chamber 7 is kept constant at least from a portion of the major surface 21 of the solid electrolyte body 2 on which the pump electrode 30 is formed to a portion of the major surface 21 on which the monitor electrode 40 and the sensor electrode 50 are formed. The width of the gas chamber 7 is given by an interval between inner walls of the first spacer 11 in a direction perpendicular both to the direction 250 in which the gas flows within the gas chamber 7 and to the thickness of the gas chamber 7, in other words, the Y-direction in FIG. 2. The width of the gas chamber 7 is kept constant at least from the portion of the major surface on which the pump electrode 30 is formed to the portion of the major surface 21 on which the monitor electrode 40 and the sensor electrode 50 are formed. In other words, there is not any object within the gas chamber 7, such as a narrow portion or a partition wall, which will decrease a dimension of the gas chamber 7 in the Z- or Y-direction within a range from the pump electrode 30 to the monitor electrode 40 or the sensor electrode 50. This ensures flow of the gas g within the gas chamber 7 without limiting diffusion thereof from the pump electrode 30 to the monitor electrode 40 or the sensor electrode 50.

The distance L1 between the pump electrode 30 and the monitor electrode 40 and the distance L2 between the pump electrode 30 and the sensor electrode 50 in the direction X (i.e., the direction 250 of flow of the gas g) are, as illustrated in FIG. 2, identical with each other.

In this embodiment, the reference electrode 80 is, as can be seen in FIGS. 1 and 4, shared among the pump cell 3, the monitor cell 4, and the sensor cell 5. In other words, the reference electrode 80 is made of a single conductor which integrally includes the reference electrode 80p constituting the pump cell 3, the reference electrode 80m constituting the monitor cell 4, and the reference electrode 80s constituting the sensor cell 5.

Next, a principle of operation of the gas sensor 1 to measure the concentration of the given gas component will be described below. The gas g, as illustrated in FIG. 1, enters the gas chamber 7 through the diffusion resistance layer 13. Since the gas g contains oxygen molecules, the oxygen molecules are removed by the pump cell 3. Specifically, dc voltage is applied between the reference electrode 80 and the pump electrode 30 to place the reference electrode at a higher electric potential. This causes the oxygen molecules to be reduced on the pump electrode 30, so that they will be oxygen ions. The oxygen ions are then pumped into the reference gas chamber 8. The concentration of oxygen in the gas chamber 7 is regulated by controlling the amount of dc voltage applied to the pump cell 3.

The gas g in which the concentration of oxygen has been decreased is then guided to the monitor cell 4 and the sensor cell 5. The gas g contains the oxygen molecules not having been removed by the pump cell 3. The monitor cell 4, thus, measures the concentration of the oxygen molecules. In the monitor cell 4, dc voltage is, as illustrated in FIG. 3, applied between the reference electrode 80 and the monitor electrode 40 to place the reference electrode 80 at a higher electric potential. This causes the oxygen molecules to be reduced on the pump electrode 30, so that they will be oxygen ions. The oxygen ions are then pumped into the reference gas chamber 8. The monitor electrode 40 is made of a Pt—Au cermet electrode which is inactive with NOx, so that an oxygen ion current flowing through the monitor cell 4 depends only on the concentration of oxygen molecules contained in the gas g, but not the concentration of NOx. The concentration of oxygen molecules contained in the gas g is, therefore, determined by measuring the oxygen ion current using the ammeter 14.

The dc voltage is also applied between the reference electrode 80 and the sensor electrode 50 in the sensor cell 5 to place the reference electrode 80 at a higher electric potential. The sensor electrode 50 is made of a Pt—Rh cermet electrode which his active to compose NOx and thus works to reduce the oxygen molecules and NOx molecules into oxygen ions. The oxygen ions are then pumped into the reference gas chamber 8. The sum of concentrations of oxygen molecules and NOx molecules contained in the gas g is, therefore, determined by measuring the oxygen ion current using the ammeter 14.

The concentration A of oxygen molecules contained in the gas g is measured using the monitor cell 4 in the above way. The concentration B that is the sum of concentrations of the oxygen molecule and the NOx molecules is determined using the sensor cell 5. The concentration A is subtracted from the concentration B to determine the concentration of NOx contained in the gas g.

The removal of oxygen from the gas g is achieved using the pump cell 3 in this embodiment, but the direction of application of voltage may be reversed to introduce oxygen from the reference gas chamber 8 into the gas g.

The operation and beneficial advantages of this embodiment will be described below.

The solid electrolyte body 2, as illustrated in FIG. 1, has the thickness d. The pump electrode 30 and the sensor electrode 50 are at the minimum distance L2 away from each other. The gas sensor 1 is designed so that the ratio (L2/d) of the minimum distance L2 to the thickness d of the solid electrolyte body 2 is three or more. In other words, the condition where the ratio is three or more is met by setting the minimum distance L2 between the pump electrode 30 and the sensor electrode 50 to be greater than the thickness d of the solid electrolyte body 2. This results in an increased resistance between the pump electrode 30 and the sensor electrode 50 to reduce a leakage of current from the pump electrode 30 to the sensor electrode 50, thus creating a required flow of electric current required by the pump cell 3. The condition where the ratio is three or more is also met by setting the thickness d of the solid electrolyte body 2 to be smaller than the distance L2 between the pump electrode 30 and the sensor electrode 50. This results in a decreased resistance between the pump electrode 30 and the reference electrode 80 constituting the pump cell 3 (i.e., a reference electrode 80$p$) to reduce a leakage of current from the pump electrode 30 to the sensor electrode 50, thereby decreasing electrical current leaking into the sensor cell 5. This improves the accuracy in measuring the concentration of the given gas component.

This enables the pump cell 3, the monitor cell 4, and the sensor cell 5 to be formed through the single solid electrolyte body 2 so that only either of the gas chamber 7 or the reference gas chamber 8 may be located between the solid electrolyte body 2 and the heater 6, thus resulting in a decrease in distance from the pump cell 3, the monitor cell 4, and the sensor cell 5 to the heater 6. This facilitates the ease with which the heater 6 heats up the pump cell 3, the sensor cell 5, and the monitor cell 4 and also results in a decrease in thickness of the gas sensor 1 in the Z-direction, which leads to a decreased size of the gas sensor 1.

In the gas sensor 1, the reference gas chamber 8 is, as can be seen in FIGS. 1 and 3, located between the heater 6 and the solid electrolyte body 2. The above described distances D1, D2, and D3 are set equal to each other.

This enables three cells: the pump cell 3, the monitor cell 4, and the sensor cell 5 to be disposed close to the heater 6. Specifically, in this embodiment, only the reference chamber 8 lies between the solid electrolyte body 2 and the heater 6, thus permitting the interval between each of the pump cell 3, the monitor cell 4, and the sensor cell 5 and the heater 6.

The pump cell 3, the monitor cell 4, and the sensor cell 5 are all located at an equal distance from the heater 6, so that thermal energy is equally transmitted from the heater to the pump cell 3, the monitor cell 4, and the sensor cell 5, thus resulting in a decrease in variation in temperature among the pump cell 3, the monitor cell 4, and the sensor cell 5 and also enabling the heater 6 to heat up the pump cell 3, the monitor cell 4, and the sensor cell 5 with a minimum consumption of power.

The gas sensor 1 of this embodiment is designed to use the single solid electrolyte body 2, the pump electrode 30, the monitor electrode 40, and the sensor electrode 50 to make the pump cell 3, the monitor cell 4, and the sensor cell 5, respectively, thereby resulting in a decrease in production cost of the gas sensor 1.

The gas chamber 7 is, as illustrated in FIGS. 1 and 2, formed by a single space which has the given thickness in the thickness-wise direction of the heater 6 (i.e., the Z-direction) and the given width. The thickness of the gas chamber 7 is kept constant at least from an area of the major surface 21 of the solid electrolyte body 2 on which the pump electrode 30 is formed to an area of the major surface 21 on which the monitor electrode 40 and the sensor electrode 50 are formed. The width of the gas chamber 7 is given by an interval between the inner walls of the first spacer 11 in a direction perpendicular both to the direction 250 in which the gas flows within the gas chamber 7 and to the thickness of the gas chamber 7, in other words, the Y-direction in FIG. 2. The width of the gas chamber 7 is kept constant at least from the area of the major surface on which the pump electrode 30 is formed to the area of the major surface 21 on which the monitor electrode 40 and the sensor electrode 50 are formed. In other words, there is not any object within the gas chamber 7, such as a narrow portion or a partition wall, which will decrease a dimension of the gas chamber 7 in the Z- or Y-direction within a range from the pump electrode 30 to the monitor electrode 40 or the sensor electrode 50. This ensures flow of the gas g from the pump electrode 30 to the monitor electrode 40 or the sensor electrode 50 within the gas chamber 7 without limiting diffusion thereof, thus enabling a change in concentration of the given gas component (i.e., NOx) in the gas g to be measured quickly, in other words, a response rate of the gas sensor 1 to be improved.

In the gas sensor 1 of this embodiment, the reference electrode 80$p$ forming the pump cell 3, the reference electrode 80$m$ forming the monitor cell 4, and the reference electrode 80$s$ forming the sensor cell 5 are made of a single conductor.

This, as illustrated in FIG. 4, eliminates the need for providing the lead 16$b$ extending from the reference electrode 80 with each of the cells, that is, enables the single lead 16$b$ to be shared among the cells. This results in a simplified structure of the gas sensor 1. In the case where the gas sensor 1 is installed in a housing to make a gas sensor assembly, a power supply member will be joined to the lead 16$b$. The above structure enables use of a single power supply member to be joined to the lead 16$b$, thereby resulting in a simplified structure of the gas sensor 1.

In this embodiment, the distance L1 between the pump electrode 30 and the monitor electrode 40 and the distance L2 between the pump electrode 30 and the sensor electrode 50 in the direction X (i.e., the direction 250 of flow of the gas g) are, as illustrated in FIG. 2, identical with each other. This will cause the gas g in which the concentration of oxygen has been reduced to reach the monitor electrode 40 and the sensor electrode 50 at substantially the same time, so that the concentration of oxygen in the gas g on the monitor electrode 40 will be substantially equal to that on the sensor electrode 50. It is, thus, possible to eliminate the concentration of oxygen accurately by subtracting, as described above, the concentration A from the concentration B, thus resulting in enhanced accuracy in measuring the concentration of the given gas component.

The gas chamber 7 is designed to have the gas g flow in the given direction 250 within the gas chamber 7. The pump electrode 30 is located upstream in the direction 250, while the monitor electrode 40 and the sensor electrode 50 are located downstream in the direction 250. The monitor electrode 40 and the sensor electrode 50 are arranged parallel to each other in the direction 250. This results in a minimized error of a difference between the output of the monitor cell 4 which indicates the concentration of oxygen remaining in the gas g after the pump cell 3 regulates the concentration of oxygen in the gas g and the output of the sensor cell 5 which indicates the concentration of oxygen corresponding to the sum of the concentration of the given gas component (i.e., NOx) and the concentration of the residual oxygen. This results in improved accuracy in determining the concentration of the given gas component (i.e., NOx).

The pump cell 3 is greater in amount of oxygen ion flowing therethrough than the monitor cell 4. It is, therefore, preferable that the pump cell 3 is heated up to a higher temperature than the monitor cell 4 or the sensor cell 5. In order to this requirement, this embodiment, as can be seen from FIG. 4, the heat-producing center of the heater 6 where the heater 6 produces heat is located closer to the pump cell 3 so as to elevate the temperature the pump cell 3 to be slightly higher than those of the monitor cell 4 and the sensor cell 5. The heat-producing center of the heater 6 is where a portion of a thermal distribution of heat emitted from the heater 6 is the highest in temperature.

As described above, this embodiment provides the gas sensor 1 which is capable of detecting a change in output from the sensor cell 5 indicative of the concentration of the given gas component at a high response rate, minimizes a variation in temperature among the pump cell 3, the monitor cell 4, and the sensor cell 5, reduces the amount of power consumed by the heater 6, and permitting the size thereof to be decreased.

Second Embodiment

Figure 5:
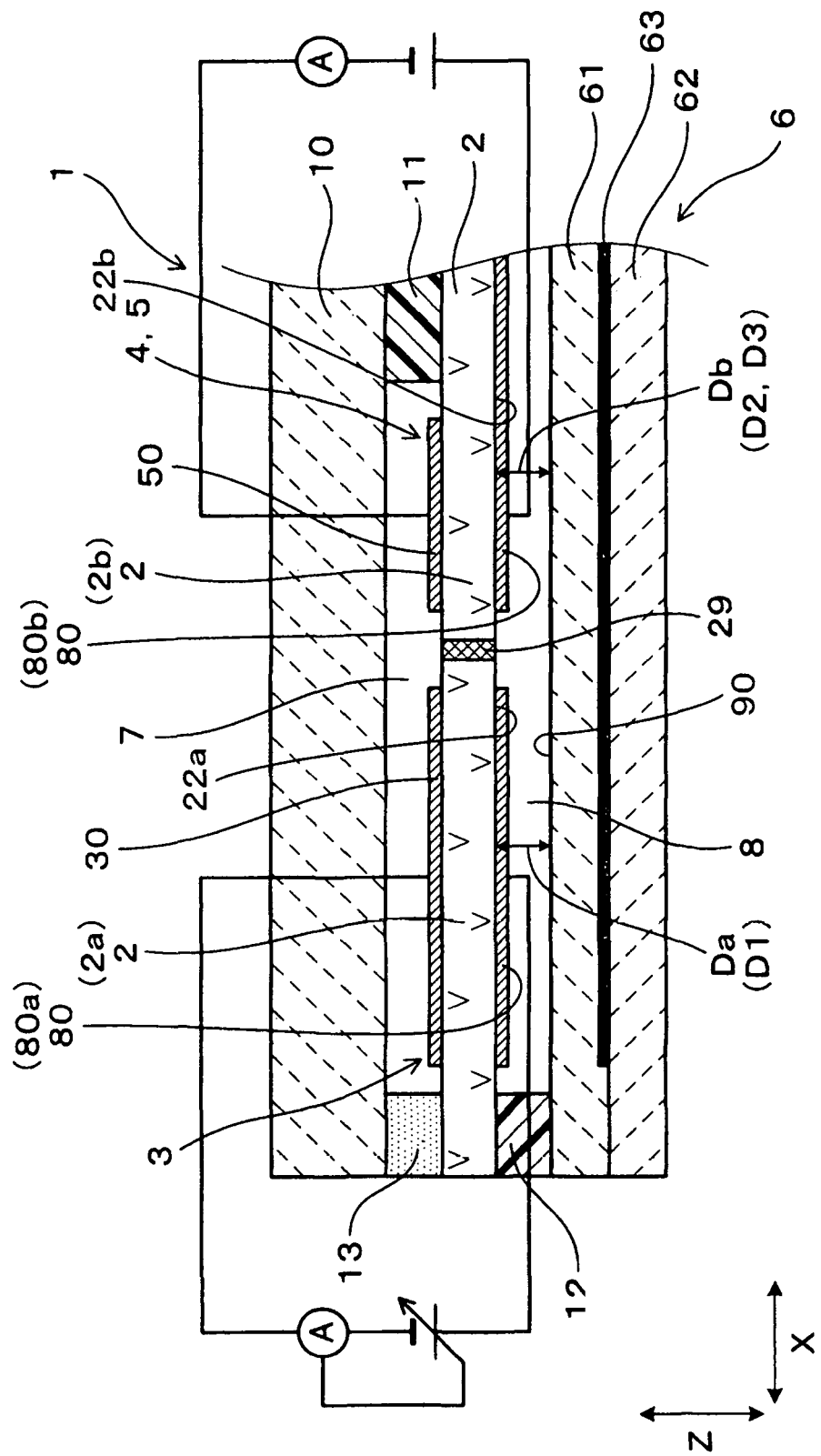
FIG. 5 is a sectional view of a gas sensor in the second embodiment.

FIG. 5 illustrates the gas sensor 1 of the second embodiment. The gas sensor 1 is equipped with a plurality of solid electrolyte bodies 2. Specifically, the gas sensor 1 includes two solid electrolyte bodies 2 (2a, 2b). The solid electrolyte body 2a forms the pump cell 3, while the solid electrolyte body 2b forms the monitor cell 4 and the sensor cell 5. The distance Da between the solid electrolyte body 2a and the heater 6 and the distance Db between the solid electrolyte body 2b and the heater 6 are equal to each other in the Z-direction. Accurately, the distance Da is a minimum distance between the major surface 22a of the solid electrolyte body 2a and the major surface 90 of the insulating layer 61 which faces the major surface 22a. The distance Db is a minimum distance between the major surface 22b of the solid electrolyte body 2b and the major surface 90 of the insulating layer 61.

The insulating member 29 is interposed between the solid electrolyte bodies 2a and 2b.

The gas sensor 1 of this embodiment is designed to use the solid electrode body 2a and the solid electrolyte body 2b which are separate from each other, one for making the pump cell 3 through which a relatively higher current flows, and the other for making the monitor cell 4 and the sensor cell 5 through which a relatively lower current flows. This minimizes a risk that a portion of current passing through the pump cell 3 flows as a noise current to the monitor cell 4 and the sensor cell 5, thus improving the accuracy in measuring the concentration of the given gas component.

Other arrangements are identical with those in the first embodiment. The same reference numbers in FIG. 5 as those in the first embodiment indicate the same parts unless otherwise specified.

Third Embodiment

Figure 6:
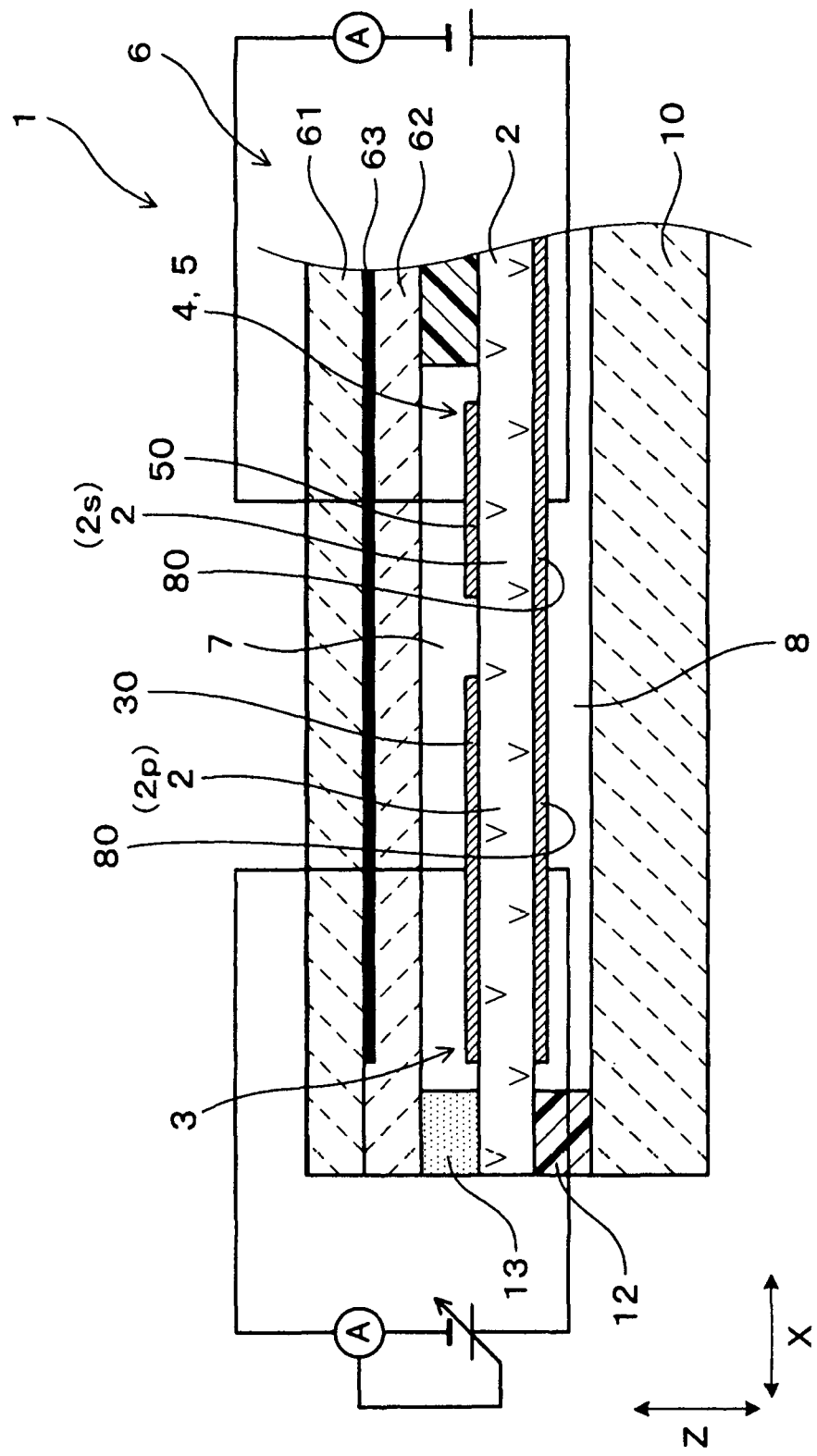
FIG. 6 is a sectional view of a gas sensor in the third embodiment.

FIG. 6 shows the gas sensor 1 in the third embodiment. The gas sensor 1 is different in location of the heater 6 from the first embodiment. Specifically, the gas chamber 7 is disposed between the heater 6 and the solid electrolyte body 2. The heater 6 faces the solid electrolyte body 2 through the gas chamber 7.

Other arrangements are identical with those in the first embodiment. The same reference numbers in FIG. 5 as those in the first embodiment indicate the same parts unless otherwise specified.

Experimental Example 1

We researched, using the gas sensor discussed in the first to third embodiments, a relation between the accuracy in measuring the concentration of NOx and the ratio (L2/d) of the minimum distance L2 between the pump electrode 30 and the sensor electrode 50 to the thickness d of the solid electrolyte body 2 for different values of the thickness d and the minimum distance L2.

Experimental tests were performed in the following way. In a gas environment in which the concentration of NOx is 100 ppm, and the concentration of $O_2$ is 20%, an electric current flowing through the sensor cell 5 which corresponds to a NOx concentration of 100 ppm is defined as a reference value (100%). The percentage of change between the reference value and a current flowing through each of samples of the gas sensor 5 which are different in dimension from each other is defined as an output error. The output error is given by a relation of output error (%)=((sensor cell current of sample/sensor cell current defined as reference value)−1)× 100.

Figures 7A, 7B:
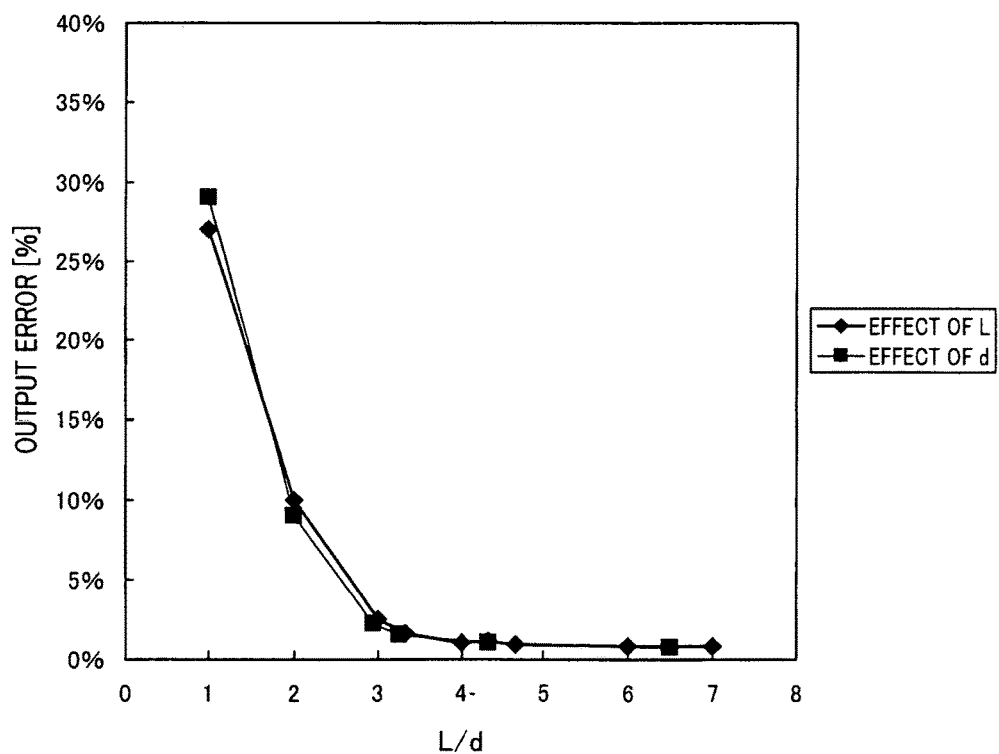
FIG. 7(a) is a table which represents experimental results about a ratio between a thickness of a solid electrolyte body and a minimum distance between a pump electrode and a sensor electrode.
FIG. 7(b) is a graph which represent experimental results about a ratio between a thickness of a solid electrolyte body and a minimum distance between a pump electrode and a sensor electrode.

FIGS. 7(a) and 7(b) represent results of the texts which show that the output error is greatly decreased to 2.5% or less by selecting the ratio (L2/d) of the minimum distance L2 between the pump electrode 30 and the sensor electrode 50 to the thickness d of the solid electrolyte body 2 to be three or more. The output error may be decreased further by setting the ratio (L2/d) to be more than three, but however, it is advisable that the ratio be seven or less in terms of the strength of the solid electrolyte body 2 or functions of the pump cell 3, the monitor cell 4, and the sensor cell 5.

EXPLANATION OF REFERENCE SIGNS

1 gas sensor
2 solid electrolyte body
3 pump cell
30 pump electrode
4 monitor cell
40 monitor electrode
5 sensor cell
50 sensor electrode
6 heater
7 gas chamber
8 reference gas chamber
80 reference electrode
100 top portion of gas sensor
g gas

The invention claimed is:

1. A gas sensor for measuring a concentration of a given gas component in oxygen-containing gas comprising:
   a gas chamber into which said gas is introduced;
   a reference gas chamber into which a reference gas is introduced;
   a single plate-like solid electrolyte body which has oxygen ion conductivity and is disposed between said gas chamber and said reference gas chamber, the solid electrolyte body having a first major surface facing said gas chamber and a second major surface facing said reference gas chamber;
   a plurality of electrodes which are formed on the first major surface of said solid electrolyte body;
   a reference electrode which is formed on the second major surface of said solid electrolyte body;
   a pump electrode which is one of said electrodes formed on the first major surface of said solid electrolyte body, the pump electrode constituting a pump cell along with said reference electrode and a portion of said solid electrolyte body, the pump cell working to regulate a concentration of oxygen in said gas;

a sensor electrode which is one of said electrodes formed on the first major surface of said solid electrolyte body, the sensor electrode constituting a sensor cell along with said reference electrode and a portion of said solid electrolyte body, the sensor cell through which a current flows which corresponds to a concentration of the given gas component in said gas after the concentration of oxygen is regulated by said pump cell; and a plate-like heater which is located so as to face said solid electrolyte body through said gas chamber or said reference gas chamber, said heater having a given thickness to heat up said solid electrolyte body, wherein dc voltage is applied to said pump cell and said sensor cell, and said current flowing through said sensor cell is measured for measuring the concentration of the given gas component, and wherein a ratio of a minimum distance between said pump electrode and said sensor electrode to a thickness of said solid electrolyte body is three or more; and wherein the gas sensor further comprises a monitor electrode which is one of said electrodes formed on the first major surface of said solid electrolyte body, the monitor electrode constituting a monitor cell along with said reference electrode and a portion of said solid electrolyte body, a current which responds to a concentration of oxygen in said gas after the concentration of oxygen is regulated by said pump cell, flowing through said monitor cell, wherein dc voltage is applied to said monitor cell, wherein a value of the current flowing through said monitor cell is subtracted from a value of the current flowing through said sensor cell to calculate the concentration of the given gas component, and wherein said gas chamber is formed by a single space.

2. A gas sensor as set forth in claim 1, wherein a distance between a surface of said heater facing said solid electrolyte body and a surface of the portion which is a portion of the second major surface of said solid electrolyte body and constitutes said pump cell in a thickness-wise direction of said heater, a distance between the surface of said heater facing said solid electrolyte body and a surface of the portion which is a portion of the second major surface of said solid electrolyte body and constitutes said monitor cell in the thickness-wise direction of said heater, and a distance between the surface of said heater facing said solid electrolyte body and a surface of the portion which is a portion of the second major surface of said solid electrolyte body and constitutes said sensor cell in the thickness-wise direction of said heater are equal to each other.

3. A gas sensor as set forth in claim 1, wherein said gas chamber is formed by a space having a given thickness in the thickness-wise direction of said heater and a given width, the thickness of said gas chamber being kept constant from a portion of said first major surface on which said pump electrode is formed to a portion of said first major surface on which said monitor electrode and said sensor electrode are formed, the width of said gas chamber being perpendicular to a direction of flow of said gas in the gas chamber and said thickness-wise direction and kept constant from the portion of the first major surface on which the pump electrode is formed to the portion of the first major surface on which the monitor electrode and the sensor electrode are formed.

4. A gas sensor as set forth in claim 1, wherein said reference electrode integrally includes a first reference electrode which forms said pump cell, a second reference electrode which forms said monitor cell, and a third reference electrode which forms said sensor cell.

5. A gas sensor as set forth in claim 1, wherein said gas chamber is designed to have said gas flow therewithin in a given direction, and wherein said pump electrode is located upstream in the given direction, while said monitor electrode and the sensor electrode are located downstream in the given direction and arranged parallel to each other.

* * * * *